United States Patent
Cathcart et al.

(10) Patent No.: US 11,257,578 B2
(45) Date of Patent: Feb. 22, 2022

(54) METHODS AND SYSTEMS FOR FACILITATING PURCHASE OF A HEALTH-RELATED PRODUCT

(71) Applicant: Cambia Health Solutions, Inc., Portland, OR (US)

(72) Inventors: Nicole Cathcart, Portland, OR (US); Max Janasik, Portland, OR (US); Alexander Thorpe, Beaverton, OR (US); Ravi Vedanayagam, Portland, OR (US); Mohan Nair, Lake Oswego, OR (US)

(73) Assignee: Cambia Health Solutions, Inc., Portland, OR (US)

( * ) Notice: Subject to any disclaimer, the term of this patent is extended or adjusted under 35 U.S.C. 154(b) by 599 days.

(21) Appl. No.: 15/890,276

(22) Filed: Feb. 6, 2018

(65) Prior Publication Data

US 2018/0233219 A1    Aug. 16, 2018

Related U.S. Application Data

(60) Provisional application No. 62/459,006, filed on Feb. 14, 2017.

(51) Int. Cl.
*G16H 20/00* (2018.01)
*G06Q 40/08* (2012.01)
(Continued)

(52) U.S. Cl.
CPC ......... *G16H 20/00* (2018.01); *G06Q 30/0207* (2013.01); *G06Q 40/08* (2013.01);
(Continued)

(58) Field of Classification Search
None
See application file for complete search history.

(56) References Cited

U.S. PATENT DOCUMENTS

| 6,616,049 B1 | 9/2003 | Barkan et al. |
|---|---|---|
| 7,566,000 B2 | 7/2009 | Agostino et al. |
| | (Continued) | |

FOREIGN PATENT DOCUMENTS

WO    WO-2010132348 A1 * 11/2010 ......... G06Q 30/0225

OTHER PUBLICATIONS

Lindley, Font-end Driven Applicants—A New Approach to Applications, https://www.telerik.com/blogs/front-end-driven-applications-new-approach-applications, Sep. 30, 2014 (Year: 2014).*

(Continued)

*Primary Examiner* — Devin C Hein
(74) *Attorney, Agent, or Firm* — McCoy Russell LLP (57) ABSTRACT

In particular, systems and methods for facilitating the purchase of health-related items such as durable medical equipment are provided. In one embodiment, a method comprises: responsive to a selection of a health-related product input by a user, automatically determining if the health-related product is a qualified healthcare expense; calculating an out-of-pocket cost to the user of the healthcare product based on a health insurance plan of the user; and generating a coupon for the health-related product that discounts a retail cost of the health-related product to the out-of-pocket cost responsive to a merchant accepting the coupon. In this way, a (Continued)

healthcare consumer may utilize their healthcare insurance benefits to purchase health-related products such as durable medical equipment from retail merchants.

20 Claims, 4 Drawing Sheets (51) Int. Cl.
G06Q 30/02 (2012.01)
G06Q 30/06 (2012.01)
G16H 10/60 (2018.01)
G16H 40/40 (2018.01)

(52) U.S. Cl.
CPC .............. *G16H 40/40* (2018.01); *G06Q 30/06* (2013.01); *G16H 10/60* (2018.01)

(56) References Cited

U.S. PATENT DOCUMENTS

| | | |
|---|---|---|
| 8,670,996 B1 | 3/2014 | Weiss |
| 8,788,281 B1 | 7/2014 | Pletz et al. |
| 2001/0034618 A1 | 10/2001 | Kessler et al. |
| 2003/0225627 A1 | 12/2003 | Mast |
| 2005/0091080 A1 | 4/2005 | Biats, Jr. |
| 2006/0190337 A1 | 8/2006 | Ayers, Jr. et al. |
| 2006/0224443 A1 | 10/2006 | Soza et al. |
| 2007/0233526 A1* | 10/2007 | Hoffman ............. G06Q 10/087 705/4 |
| 2011/0015978 A1 | 1/2011 | Welch, Jr. |
| 2012/0209686 A1* | 8/2012 | Horowitz ........... G06Q 30/0633 705/14.26 |
| 2013/0144715 A1 | 6/2013 | Kranzley et al. |
| 2013/0191205 A1 | 7/2013 | Harkless, II et al. |
| 2013/0332199 A1* | 12/2013 | Freiwat .................. G06Q 40/08 705/4 |
| 2015/0379552 A1 | 12/2015 | Kent et al. |

OTHER PUBLICATIONS

Cener for Consumer Information and Insurance Oversight, Essential Health Benefits Bulletin, Dec. 16, 2011, https://www.cms.gov/CCIIO/Resources/Files/Downloads/essential_health_benefits_bulletin.pdf, pp. 4-5 and 7 (Year: 2011).*

Levinson (Manufacturer Safeguards May Not Prevent Copayment Coupon Use for Part D Drugs), Sep. 2014, Department of Health and Human Services, OEI-05-12-00540 (Year: 2014).*

"Shopkick Mobile App," Shopkick Website, Available Online at https://web.archive.org/web/20100805210438/http://www.shopkick.com:80/app.html, Available as Early as Aug. 5, 2010, 3 pages.

"Pirq: How it Works," Pirq Website, Available Online at https://web.archive.org/web/20110424114734/http://pirq.com:80/how_it_works, Available as Early as Apr. 24, 2011, 1 page.

"FrontFlip Website Homepage," FrontFlip Website, Available Online at https://web.archive.org/web/20111007201139/http://www.frontflip.com/, Available as Early as Oct. 7, 2011, 2 pages.

"Ibotta: You Earned It," Ibotta Website, Available Online at https://web.archive.org/web/20130102005206/https://ibotta.com/, Available as Early as Jan. 2, 2013, 2 pages.

"Healthcare in a Jiff," Jiff Website, Available Online at https://web.archive.org/web/20130310040102/https://www.jiff.com/, Available as Early as Mar. 10, 2013, 1 page.

"Woobox: Coupons & Vouchers," Woobox Website, Available Online at https://web.archive.org/web/20130311222308/https://woobox.com/coupons, Available as Early as Mar. 11, 2013, 4 pages.

"Target Cartwheel: A whole new spin on coupons," Target Cartwheel Website, Available Online at https://web.archive.org/web/20130508141135/https://cartwheel.target.com/, Available as Early as May 8, 2013, 4 pages.

"Walmart's Savings Catcher," Walmart's Savings Catcher Website, Available Online at https://web.archive.org/web/20140314184750/https://savingscatcher.walmart.com/, Available as Early as Mar. 14, 2014, 2 pages.

* cited by examiner

METHODS AND SYSTEMS FOR FACILITATING PURCHASE OF A HEALTH-RELATED PRODUCT

CROSS REFERENCE TO RELATED APPLICATION

The present application claims priority to U.S. Provisional Application No. 62/459,006, entitled "METHODS AND SYSTEMS FOR FACILITATING PURCHASE OF A HEALTH-RELATED PRODUCT," filed Feb. 14, 2017, the entire contents of which is hereby incorporated by reference in its entirety for all purposes.

BACKGROUND AND SUMMARY

Healthcare in the United States is the most expensive in the world and is regularly ranked last among similar countries for the quality of healthcare. Over $8,000 per capita on healthcare services in the United States in 2011. Most of the time, consumers do not have any idea how much their healthcare may cost prior to treatment. Consumers are not encouraged to compare costs for treatments and services and they are not encouraged to look for referral options. The cost for treatments and services varies widely from doctor to doctor and from facility to facility. For example, prices for common services, such as Mills, can vary by thousands of dollars across different regions of the country, within the same metro areas, and even across hospitals and clinics that share the same healthcare providers.

The low transparency of the healthcare marketplace also extends to durable medical equipment (DME). Currently, the experience of shopping for DME is fragmented and the healthcare consumer is generally left alone to navigate the process of obtaining DME. Further, there is typically no retail pricing or cost transparency. Consumers must determine what they need, where they can obtain what they need, what is DME and what is in network, what is HSA eligible, what do their benefits cover, and so on. A consumer is prescribed a DME by a doctor. Either the doctor orders the DME or the consumer has to find an in-network DME vendor. In the latter case, the consumer has to call his or her health plan for vendor recommendations and to determine the consumer's cost share. The reimbursement difference is charged to the consumer, mostly days or even weeks after receipt of the item. Contracted DME vendors do not advertise prices or allow for online shopping. Consumers are not clear on their responsibility without significant effort (e.g., calling customer service and multiple vendors).

The processes for reimbursement and billing for DME is currently arduous for the consumer. Consumer price shops, finds the best price for item, and pays the full cost of the DME up front. The consumer may then log into member portal or calls customer service to find a PDF reimbursement form somewhere on the health plan website. The consumer fills out the form, attaches the receipt, and mails or faxes the paperwork to customer service. If the form is correct, the consumer receives reimbursement for their cost share in the mail 4-6 weeks later. If there are any problems in the process, the consumer must start the process again. There are limited electronic submission capabilities and an arduous back-office process of scanning and manually entering information. The consumer has no way to get status transparency or expedite the process unless they call customer service.

The inventors have recognized the above issues and have devised several approaches to address them. In particular, systems and methods for facilitating the purchase of durable medical equipment are provided. In one embodiment, a method comprises: responsive to a selection of a healthcare product input by a user, automatically determining if the healthcare product is a qualified healthcare expense; calculating an out-of-pocket cost to the user of the healthcare product based on a health insurance plan of the user; and generating a coupon for the healthcare product that discounts a retail cost of the healthcare product to the out-of-pocket cost responsive to a merchant accepting the coupon. In this way, a healthcare consumer may utilize their healthcare insurance benefits to purchase healthcare products such as durable medical equipment from retail merchants.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The present description relates to systems and methods for facilitating purchase of health-related products. In particular, systems and methods for automatically generating coupons and medical claims for health-related items or goods such as durable medical equipment (DME) are provided. The methods and systems described herein enable in-store retail and online purchases with real-time benefits integration and claims submission. Advantageously, the methods and systems described herein enable consumer choice across preferred retailers, and drastically simplifies the experience of obtaining DME.

Figure 1:
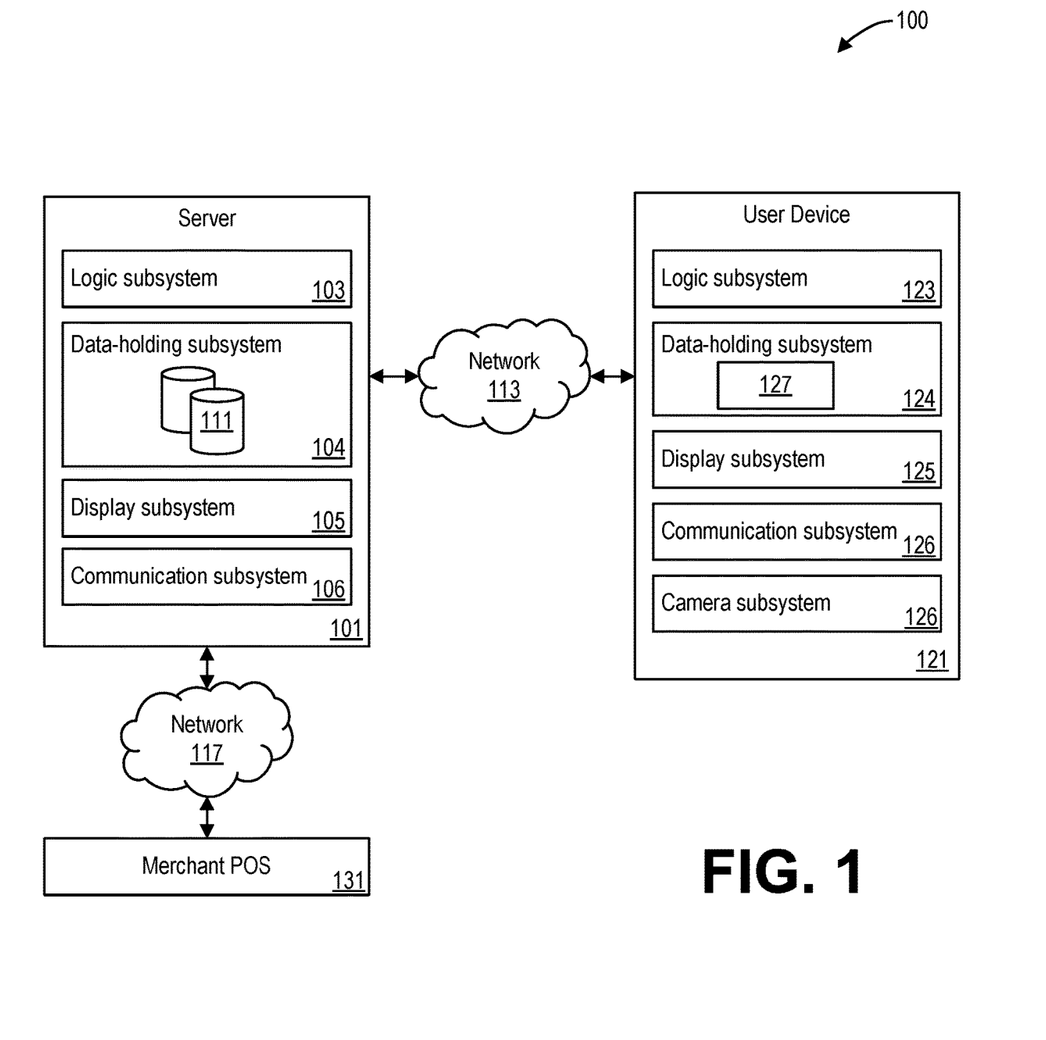
FIG. 1 illustrates an overview of an exemplary computing environment according to an embodiment.

FIG. 1 illustrates an example computing environment 100 in accordance with the current disclosure. In particular, computing environment 100 includes a server 101, a user device 121, a merchant point-of-sale (POS) device 131, and networks 113 and 117. However, not all of the components illustrated may be required to practice the invention. Variations in the arrangement and type of the components may be made without departing from the spirit or scope of the invention.

Server 101 may be a computing device configured to automatically generate healthcare claims and facilitate transfer of funds responsive to the use of a coupon. In different embodiments, server 101 may take the form of a mainframe computer, server computer, desktop computer, laptop computer, tablet computer, home entertainment computer, network computing device, mobile computing device, mobile communication device, gaming device, etc.

Server 101 includes a logic subsystem 103 and a data-holding subsystem 104. Server 101 may optionally include a display subsystem 105, communication subsystem 106, and/or other components not shown in FIG. 1. For example, server 101 may also optionally include user input devices such as keyboards, mice, game controllers, cameras, microphones, and/or touch screens.

Logic subsystem 103 may include one or more physical devices configured to execute one or more instructions. For example, logic subsystem 103 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 103 may include one or more processors that are configured to execute software instructions. Additionally or alternatively, the logic subsystem 103 may include one or more hardware or firmware logic machines configured to execute hardware or firmware instructions. Processors of the logic subsystem 103 may be single or multi-core, and the programs executed thereon may be configured for parallel or distributed processing. The logic subsystem 103 may optionally include individual components that are distributed throughout two or more devices, which may be remotely located and/or configured for coordinated processing. One or more aspects of the logic subsystem 103 may be virtualized and executed by remotely accessible networked computing devices configured in a cloud computing configuration.

Data-holding subsystem 104 may include one or more physical, non-transitory devices configured to hold data and/or instructions executable by the logic subsystem 103 to implement the herein described methods and processes. When such methods and processes are implemented, the state of data-holding subsystem 104 may be transformed (for example, to hold different data).

Data-holding subsystem 104 may include removable media and/or built-in devices. Data-holding subsystem 104 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 104 may include devices with one or more of the following characteristics: volatile, nonvolatile, dynamic, static, read/write, read-only, random access, sequential access, location addressable, file addressable, and content addressable. In some embodiments, logic subsystem 103 and data-holding subsystem 104 may be integrated into one or more common devices, such as an application-specific integrated circuit or a system on a chip.

It is to be appreciated that data-holding subsystem 104 includes one or more physical, non-transitory devices. In contrast, in some embodiments aspects of the instructions described herein may be propagated in a transitory fashion by a pure signal (for example, an electromagnetic signal) that is not held by a physical device for at least a finite duration. Furthermore, data and/or other forms of information pertaining to the present disclosure may be propagated by a pure signal.

When included, display subsystem 105 may be used to present a visual representation of data held by data-holding subsystem 104. As the herein described methods and processes change the data held by the data-holding subsystem 104, and thus transform the state of the data-holding subsystem 104, the state of display subsystem 105 may likewise be transformed to visually represent changes in the underlying data. Display subsystem 105 may include one or more display devices utilizing virtually any type of technology. Such display devices may be combined with logic subsystem 103 and/or data-holding subsystem 104 in a shared enclosure, or such display devices may be peripheral display devices.

When included, communication subsystem 106 may be configured to communicatively couple server 101 with one or more other computing devices, such as user device 121 and/or merchant POS device 131. Communication subsystem 106 may include wired and/or wireless communication devices compatible with one or more different communication protocols. As non-limiting examples, communication subsystem 106 may be configured for communication via a wireless telephone network, a wireless local area network, a wired local area network, a wireless wide area network, a wired wide area network, etc. In some embodiments, communication subsystem 106 may allow server 101 to send and/or receive messages to and/or from other devices via a network such as the public Internet. For example, communication subsystem 106 may communicatively couple server 101 with user device 121 via network 113 and/or merchant POS device 131 via network 117. In some examples, network 113 may be the public Internet. Furthermore, network 117 may be regarded as a private network connection and may include, for example, a virtual private network or an encryption or other security mechanism employed over the public Internet. In some examples, network 113 and network 117 may be the same network.

Computing environment 100 may include one or more devices operated by users, such as user device 121. User device 121 may be any computing device configured to access a network such as network 113, including but not limited to a personal computer, a laptop, a smartphone, a tablet, and the like.

User device 121 includes a logic subsystem 123 and a data-holding subsystem 124. User device 121 may optionally include a display subsystem 125, communication subsystem 126, and/or other components not shown in FIG. 1. For example, user device 121 may also optionally include user input devices such as keyboards, mice, game controllers, cameras, microphones, and/or touch screens.

Logic subsystem 123 may include one or more physical devices configured to execute one or more instructions. For example, logic subsystem 123 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 123 may include one or more processors that are configured to execute software instructions. Additionally or alternatively, the logic subsystem 123 may include one or more hardware or firmware logic machines configured to execute hardware or firmware instructions. Processors of the logic subsystem 123 may be single or multi-core, and the programs executed thereon may be configured for parallel or distributed processing. The logic subsystem 123 may optionally include individual components that are distributed throughout two or more devices, which may be remotely located and/or configured for coordinated processing. One or more aspects of the logic subsystem 123 may be virtualized and executed by remotely accessible networking computing devices configured in a cloud computing configuration.

Data-holding subsystem 124 may include one or more physical, non-transitory devices configured to hold data and/or instructions executable by the logic subsystem 123 to implement the herein described methods and processes. When such methods and processes are implemented, the state of data-holding subsystem 124 may be transformed (for example, to hold different data).

Data-holding subsystem 124 may include removable media and/or built-in devices. Data-holding subsystem 124 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 124 may include devices with one or more of the following characteristics: volatile, nonvolatile, dynamic, static, read/write, read-only, random access, sequential access, location addressable, file addressable, and content addressable. In some embodiments, logic subsystem 123 and data-holding subsystem 124 may be integrated into one or more common devices, such as an application-specific integrated circuit or a system on a chip.

When included, display subsystem 125 may be used to present a visual representation of data held by data-holding subsystem 124. As the herein described methods and processes change the data held by the data-holding subsystem 124, and thus transform the state of the data-holding subsystem 124, the state of display subsystem 125 may likewise be transformed to visually represent changes in the underlying data. Display subsystem 125 may include one or more display devices utilizing virtually any type of technology. Such display devices may be combined with logic subsystem 123 and/or data-holding subsystem 124 in a shared enclosure, or such display devices may be peripheral display devices.

When included, communication subsystem 126 may be configured to communicatively couple user device 121 with one or more other computing devices, such as server 101. Communication subsystem 126 may include wired and/or wireless communication devices compatible with one or more different communication protocols. As non-limiting examples, communication subsystem 126 may be configured for communication via a wireless telephone network, a wireless local area network, a wired local area network, a wireless wide area network, a wired wide area network, etc. In some embodiments, communication subsystem 126 may allow user device 101 to send and/or receive messages to and/or from other devices, such as server 101, via a network 113 such as the public Internet.

Similarly, merchant POS device 131 may comprise a computing device communicatively coupled to server 101 via network 117. In some examples, server 101 may include one or more databases 111 that contain claims data, where the claims data may include information regarding health care treatments, services, costs, and so on, as well as benefits for users. In some examples, one or more databases of the one or more databases 111 may store coupon information for authentication.

Thus server 101, user device 121, and merchant POS device 131 may each represent computing devices which may generally include any device that is configured to perform computation and that is capable of sending and receiving data communications by way of one or more wired and/or wireless communication interfaces. Such devices may be configured to communicate using any of a variety of network protocols. For example, user device 121 may be configured to execute an application 124 that employs HTTP or another protocol to request information from server 101 and then displays the retrieved information to a user on a display such as the display subsystem 125.

Server 101 may collect and process data from user device 121 and merchant POS device 131. Server 101 may analyze the collected data using, for example, data analysis techniques and/or artificial intelligence techniques.

Figure 2:
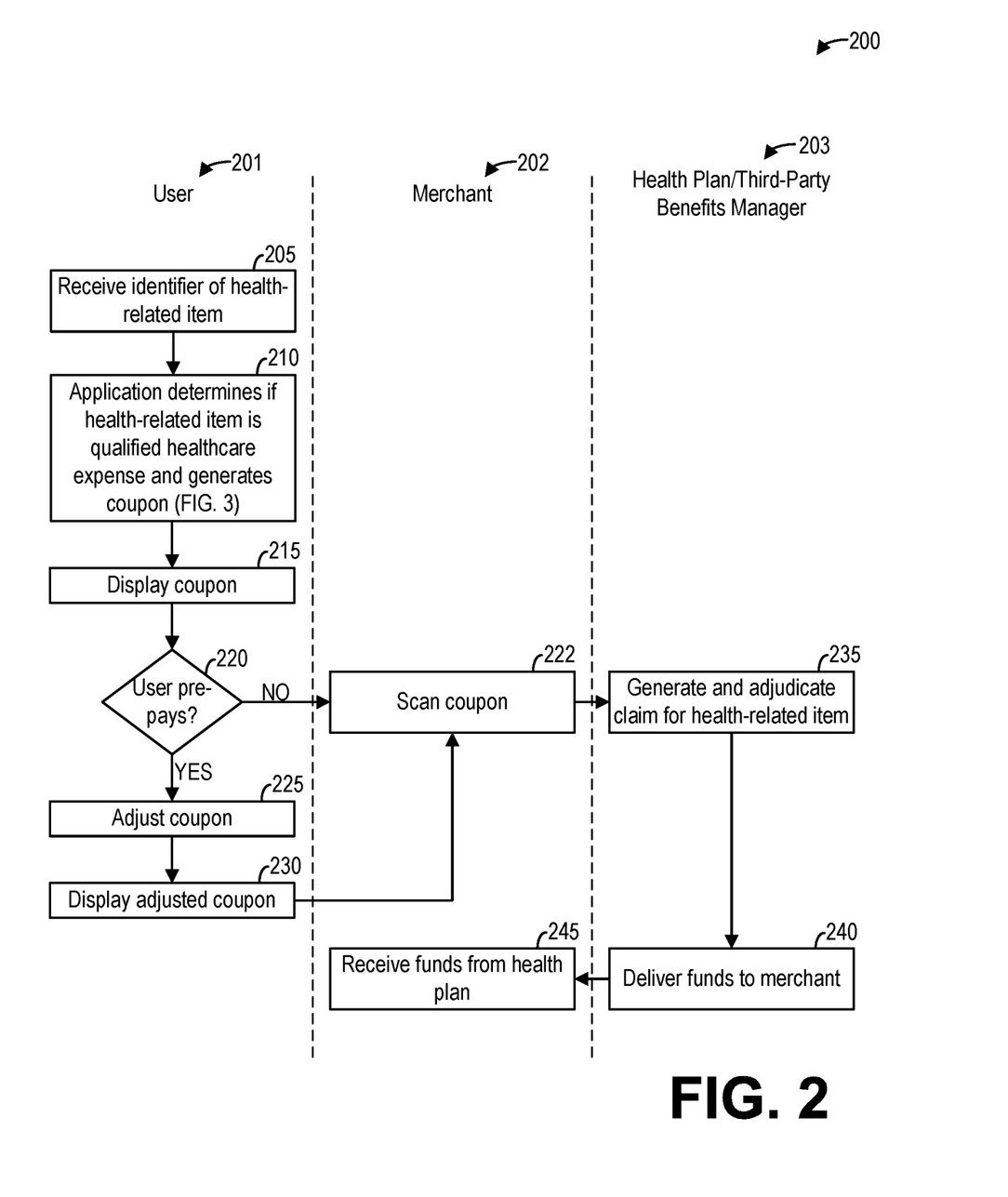
FIG. 2 shows a high-level swim lane flow chart illustrating an example method for purchasing health-related goods according to an embodiment.

FIG. 2 shows a high-level swim lane flow chart illustrating an example method 200 for facilitating a purchase of a health-related product. Specifically, the method 200 facilitates a purchase by a user 201 of a health-related product from a merchant 202 with at least part of the cost of the health-related product covered by a health plan or a third-party benefits manager 203. The method 200 is described herein with regard to the systems and components depicted in FIG. 1, though it should be understood that the method may be implemented with other systems and components without departing from the scope of the present disclosure. For example, one or more steps carried out by the user 201 may be carried out via a user device 121, one or more steps carried out by the merchant 202 may be carried out via a merchant POS device 131, and one or more steps carried out by the health plan or third-party benefits manager 203 may be carried out via a server 101.

Method 200 may begin at 205. At 205, the user 201 scans the barcode of a health-related item. For example, the user 201 may notice a health-related item in a store that could be HSA-qualified or covered by healthcare benefits. To determine whether the health-related item is a qualified healthcare expense that may be at least partially covered by the user's health insurance, the user 201 opens an application on the user device 121, such as application 127, and scans the barcode of the health-related item.

At 210, the application of the user device determines if the health-related item is a qualified healthcare expense and generates a coupon. A method for determining if the health-related item is a qualified healthcare expense and generating a coupon is described further herein with regard to FIG. 3. Coupons are thus generated in real-time for instant delivery to the user device. The coupon may be time-bound to expire within a designated period. For example, the coupon may be designated to expire within ten days, or in other examples, within a time period greater than or less than ten days. The coupon system is also merchant-agnostic, such that any merchant that sells DME products and utilizes a digital coupon system may participate in the methods described herein.

A unique identifier, such as a barcode, generated with the coupon is available for a single use by the particular user who initiated the generation of the coupon. The coupons are available only for designated member use, and are authenticated in real-time to a single member/subscriber. It should be appreciated that a "member" may comprise a designated family healthcare manager and/or an authorized caregiver, in addition to or as an alternative to the person covered by the health plan. In some examples, the application 127 may include an aggregated family view such that multiple persons who may carry out a purchase of a health-related item for a person, such as a designated family healthcare manager, authorized caregiver, and/or the person for whom the health-related item is intended, can utilize the application 127 as described herein.

At 215, the coupon is displayed, for example, via the display subsystem 125 of the user device 121. The coupon may include a unique identifier such as a barcode and/or a unique number that may be displayed via the display subsystem so that the unique identifier associated with the coupon may be scanned or manually input by the merchant.

To that end, in some examples, the unique identifier may be represented by an optical, machine-readable representation of data that is one-dimensional (e.g., a barcode), two-dimensional (e.g., a quick response or QR code), and the like. As another example, the unique identifier may be transmitted or scanned via an RFID tag. Alternatively, the barcode and/or unique number (e.g., coupon code) may be manually input by the user online on the merchant's website should the user prefer to complete the transaction online. In some examples, the unique identifier identifies one or more of the user, the health-related product, and the out-of-pocket cost of the healthcare product. In general, it should be appreciated that the method may utilize any suitable means for representing or transmitting the unique identifier identifying the coupon.

At 220, method 200 determines if the user 201 has pre-paid for the health-related item. For example, the coupon generated at 210 may include an indication of an out-of-pocket cost for the user 201 for the health-related item. The user 201 may select to pay the out-of-pocket cost upfront through the application 127, for example. For example, the application 127 may include an online payment system that allows the user 201 to input debit or credit card information, bank account routing information, and/or an electronic money transfer account information (such as PayPal, as a non-limiting example), thereby enabling the user to transfer the out-of-pocket cost from a financial account of the user 201 to an account of the health plan or third-party benefits manager 203.

If the user 201 has not pre-paid for the health-related item ("NO"), method 200 continues to 222. However, if the user 201 has pre-paid for the health-related item ("YES"), method 200 continues to 225. At 225, method 200 adjusts the coupon generated at 210 such that the adjusted coupon covers the full listed retail cost of the health-related item. For example, the logic subsystem 123 of the user device 121 may, via the application 127, adjust the coupon. At 230, method 200 displays the adjusted coupon. For example via display subsystem 125. In this way, the user 201 may redeem the adjusted coupon with the merchant 202 in exchange for the health-related item without directly paying the merchant 202. After displaying the adjusted coupon at 230, method 200 continues to 222.

At 222, the merchant 202 scans the coupon using the merchant point-of-sale (POS) system, such as merchant POS 131, which includes a subsystem for handling coupons. Alternatively, as discussed further herein, at 222, the user 201 may input the coupon code of the coupon to the online marketplace of the merchant 202. In one example, the coupon indicates that the user 201 is responsible for at least a portion of the retail cost of the health-related item, while the user's health plan or third-party benefits manager 203 is responsible for the remaining cost of the health-related item. Upon scanning the coupon, the merchant POS 131 communicates to the server 101 of the health plan or third-party benefits manager 203 that the user 201 is purchasing the health-related item from the merchant 202. Further, the merchant POS 131 may communicate with the server 101 of the health plan or third-party benefits manager 203 to determine that the coupon is valid (e.g., has not been used or expired).

Responsive to receiving the indication from the merchant 202 that the coupon is scanned, at 235, the health plan or third-party benefits manager 203 generates and adjudicates a healthcare claim for the health-related item. At 240, the health plan or third-party benefits manager 203 delivers funds to the merchant 202. Funds are delivered to the merchant 202 via existing coupon rails. Utilizing the pre-existing coupon system simplifies the merchant's commitment. The amount of funds delivered to the merchant 202 includes an amount of funds covered by the health plan 203 of the user 201, and may further include the pre-payment of the user 201 for the out-of-pocket cost for the user 201 if the user 2021 opted to pre-pay at 220.

It should be appreciated that in examples wherein the health plan 203 does not owe money, the transaction total and the member details may still be collected to count against the deductible.

At 245, the merchant 202 receives the funds from the health plan or third-party benefits manager 203 and the remaining cost from the user 201. The user 201 pays their remaining cost share at check-out if they did not pre-pay. In some examples, the health plan or third-party benefits manager 203 delivers the funds to the merchant 202 in real-time, though in other examples, the health plan third-party benefits manager 203 delivers funds to the merchant 202 in batches so the funds may not be delivered in real-time. Method 200 then ends.

Figure 3:
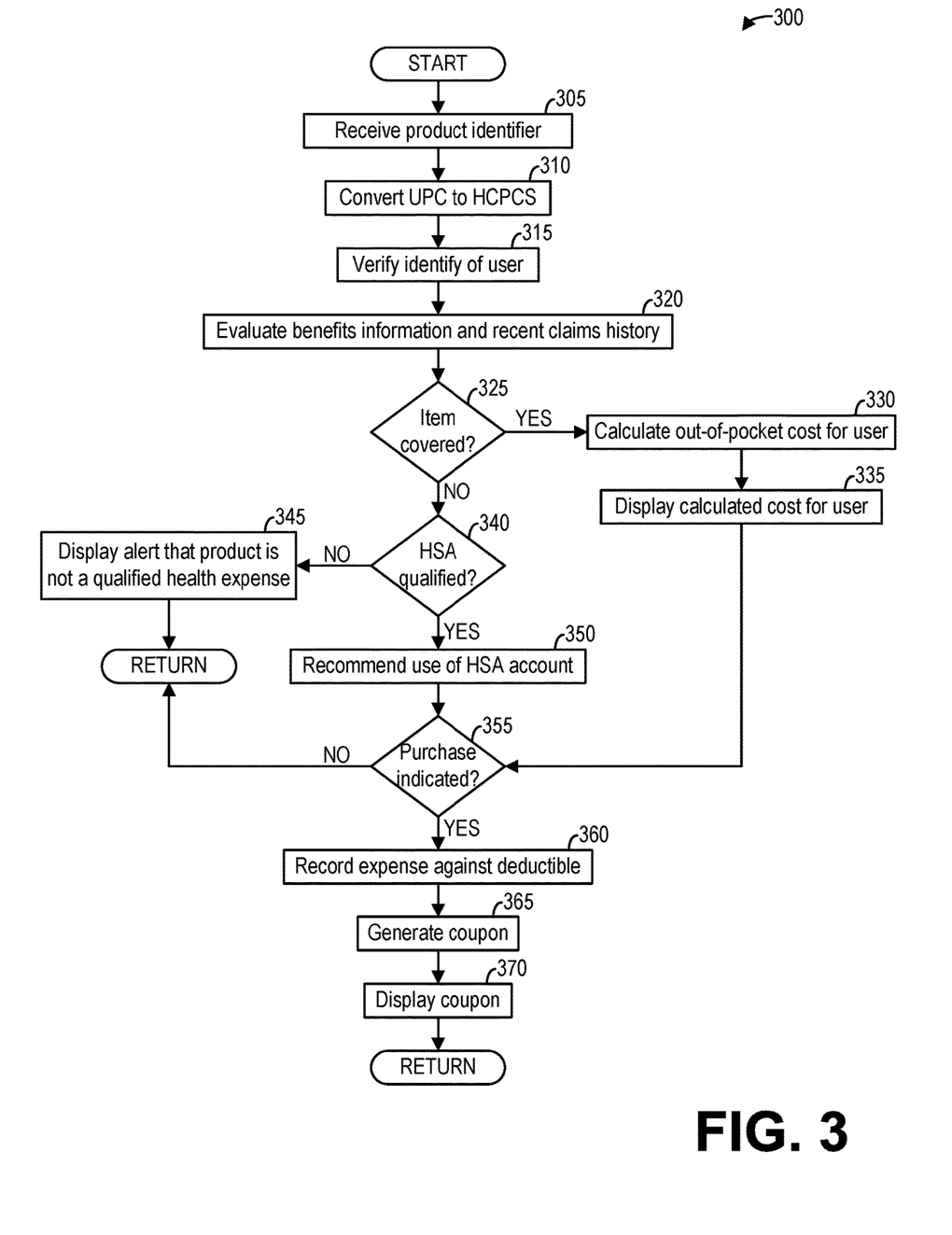
FIG. 3 shows a high-level flow chart illustrating an example method for generating a coupon for a health-related good according to an embodiment.

FIG. 3 shows a high-level flow chart illustrating an example method 300 for generating a coupon for a health-related good according to an embodiment. In particular, method 300 relates to providing a coupon for a consumer to pay an adjusted price for a health-related good based on whether the health-related good is a qualified healthcare expense. Method 300 is described herein with regard to the systems and components depicted in FIG. 1, though it should be appreciated that the method may be implemented with other systems and components without departing from the scope of the present disclosure. For example, method 300 may be stored as executable instructions in non-transitory memory, such as data-holding subsystem 124, and executed by a processor, such as logic subsystem 123, of a user device such as user device 121.

Method 300 may begin at 305. At 305, method 300 receives a product identifier for a health-related item or product. In one example, receiving a product identifier comprises scanning a barcode, as a non-limiting example, of a healthcare good such as a DME product. For example, the method scans the barcode using a camera subsystem such as camera subsystem 126. The barcode typically includes a Universal Product Code (UPC) that uniquely identifies the product. Alternatively, receiving a product identifier for a healthcare product may include receiving a URL that points to a product page for a healthcare product in an online retail marketplace. The product page may include a product identifier such as a UPC; the method may automatically retrieve said product identifier from the product page.

At 310, method 300 converts the UPC to the corresponding Healthcare Common Procedure Coding System (HCPCS) code or another suitable medical coding system code. The UPC comprises a 12 numerical digit number that uniquely identifies the particular DME product, while the HCPCS code comprises an alphanumeric medical procedure code that characterizes a DME product. For example, HCPCS codes for DME products typically begin with an "E" followed by a four numerical digit number. As an example, the HCPCS code E0100 corresponds to a cane, including canes of all materials, adjustable or fixed, with a tip, whereas the HCPCS code E0105 corresponds to a cane, quad or three prong, including canes of all materials, adjustable or fixed, with tips. As another example, the HCPCS code E0602 corresponds to a manual breast pump of any type, the HCPCS code E0603 corresponds to an electric (AC and/or DC) breast pump of any type, and the HCPCS code E0605 corresponds to a hospital-grade electric (AC and/or DC) breast pump of any type.

Since HCPCS codes comprise general categories for DME products, there is generally not a one-to-one mapping between UPCs and HCPCS codes. For example, the UPC of the BellaMa Effective Pro Double Electric Breast Pump with Independent Dual Control is 713382716000, and the UPC of the BellaMa Melon Comfort Double/Single Electric Breast Pump is 713382715966; both products are categorized under the HCPCS code E0603.

To convert the UPC to HCPCS code, the method may access a database or another data structure (e.g., look-up table) that associates UPCs of healthcare products with corresponding HCPCS code(s). For example, if the barcode of either of the breast pump products discussed hereinabove is scanned, the method may access the database, and look up the HCPCS code that corresponds to the UPC of the product. The HCPCS code may be used later to generate a healthcare claim, as well as to initially verify that the product associated with the scanned barcode is a healthcare product.

It should be appreciated that the healthcare product is not limited to a DME product that has an HCPCS code beginning with E. In some examples, the healthcare product may include medical supplies with corresponding HCPCS codes that begin with A4, A5, A6, A7, A9, B4, B5, B9, C2, E, K, L, Q, S8, and/or V. The Centers for Medicare & Medicaid Services (CMS) maintains an updated list of HCPCS codes for medical supplies, and one of ordinary skill in the art may refer to said list for a complete view of what comprises a healthcare product as defined herein. As some illustrative and non-limiting examples, the HCPCS code for wheelchairs may comprise E0950 through E1030, E1050 through E1298, E2300 through E2399, or K0001 through K0109; the HCPCS code for an adhesive bandage is A6413; the HCPCS code for an amputee stump sock may comprise L8470 through L8485; the HCPCS codes for cast supplies may comprise A4580, A4590, and/or Q4001 through Q4051; and the HCPCS codes for a continuous glucose monitoring system receiver, sensor, and transmitter are respectively A9278, A9276, and A9277.

At 315, method 300 verifies the identity of the user, for example, by communicating with the health plan server, such as server 101, to authenticate the user's insurance benefits eligibility and retrieve benefits information and recent claims history. At 320, method 300 evaluates benefits information and recent claims history. For example, the method may determine if there is a relevant diagnosis and/or prescription for the DME product in the recent claims history, and may further determine if the health plan benefits of the user covers the DME product.

At 325, method 300 determines if the item is covered by the user's health care benefits. Coverage of the item may be determined based on the HCPCS, the UPC, the health care benefits for the user, and the recent claims history for the user. For example, ten UPCs may be associated with one HCPCS code, but three of the UPCs may for some reason not be covered despite having an associated HCPCS code. As another example, the health care benefits may cover a product, but if the user has not received a prescription for the product or a relevant diagnosis, then the benefits may not cover the purchase. If the item is covered ("YES"), method 300 proceeds to 330. At 330, method 300 calculates the out-of-pocket cost of the item for the user. At 335, method 300 displays the calculated cost for the user. In some examples, the user may manually input the listed retail price of the DME product in order to obtain the out-of-pocket cost of the product. Method 300 then proceeds to 355.

Referring again to 325, if the item is not covered ("NO"), method 300 proceeds to 340. At 340, method 300 determines if the item is a qualified expense for a Health Savings Account (HSA) or another similar medical savings account. If the item is not HSA qualified ("NO"), method 300 proceeds to 345. At 345, method 300 displays an alert that the product is not a qualified health expense. No coupon is generated, and method 300 returns.

However, referring again to 340, if the item is HSA qualified ("YES"), method 300 proceeds to 350. At 350, method 300 recommends use of the HSA account. For example, the method may display an indication that the product is not covered by the health care benefits but is HSA qualified. Method 300 then proceeds to 355.

At 355, method 300 determines if a purchase is indicated. For example, if the user decides to purchase the item and utilize the HSA account or the healthcare benefits, the user may indicate, via the application on the user device, to order the item for purchase. If a purchase is not indicated ("NO"), method 300 returns. However, if a purchase is indicated ("YES"), method 300 proceeds to 360. At 360, method 300 records the expense against the deductible.

Continuing at 365, method 300 generates a digital coupon that administers healthcare benefits for the user. In some examples, the coupon may comprise a unique voucher entitling the holder to a discount for a particular product based on the healthcare benefits of the holder, while in other examples, the coupon may comprise a voucher that functions as a proof-of-purchase to count against a deductible. The coupon may be generated with a unique code or identifier intended for single use. Such a generated coupon is available only for designated member use. To that end, the coupon may be authenticated in real-time to a single member or user. If the item is not covered but is HSA qualified, the generated coupon may be scanned as a proof-of-purchase. If the item is covered, the generated coupon may be scanned to discount the item based on the user's coverage.

At 370, method 300 displays the coupon. For example, the coupon may be displayed via the display subsystem 125 of the user device 121 such that a merchant may scan the coupon with the merchant POS device 131. In examples wherein the user is purchasing the healthcare product from an online marketplace, the coupon may comprise an alphanumeric code, as a non-limiting example, that the user may input during checkout at the online marketplace to obtain the discount or validate the proof-of-purchase. Method 300 then returns.

Figure 4:
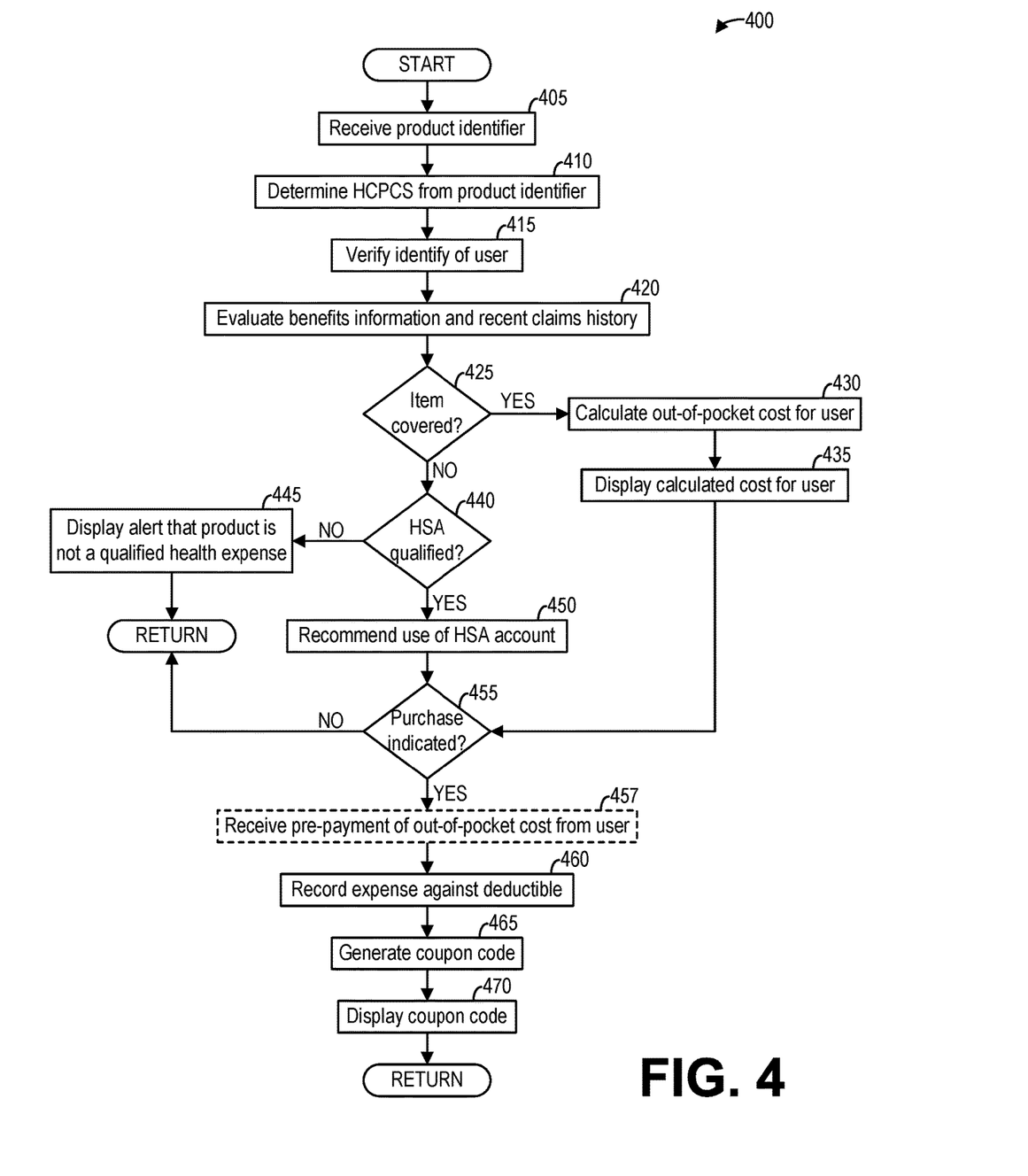
FIG. 4 shows a high-level flow chart illustrating an example method for purchasing health-related goods from an online retailer according to an embodiment.

FIG. 4 shows a high-level flow chart illustrating an example method 400 for generating a coupon for a health-related good for redemption with an online retailer or merchant according to an embodiment. In particular, method 400 relates to providing a coupon for a consumer to pay an adjusted price for a health-related good based on whether the health-related good is a qualified healthcare expense. Method 400 is described herein with regard to the systems and components depicted in FIG. 1, though it should be appreciated that the method may be implemented with other systems and components without departing from the scope of the present disclosure. For example, method 400 may be stored as executable instructions in non-transitory memory, such as data-holding subsystem 124, and executed by a processor, such as logic subsystem 123, of a user device such as user device 121.

Method 400 may begin at 405. At 305, method 300 receives a product identifier for a health-related item or product. In one example, receiving a product identifier comprises receiving, from a user via a user interface of the user device 121, a UPC or another unique identifier of a healthcare good or healthcare item such as a DME product. In another example, receiving a product identifier for a healthcare product comprises receiving a URL that points to a product page for a healthcare product in an online retail marketplace. The product page may include a product identifier such as a UPC; the method may automatically retrieve said product identifier from the product page.

At 410, method 400 determines a corresponding Healthcare Common Procedure Coding System (HCPCS) code or another suitable medical coding system code from the product identifier received at 405. For example, as discussed above, to convert the UPC to HCPCS code, the method 400 may access a database or another data structure (e.g., look-up table) that associates UPCs of healthcare products with corresponding HCPCS code(s). For example, if the UPC of either of the breast pump products discussed hereinabove is input to the application 127, the method 400 may access the database, and look up the HCPCS code that corresponds to the UPC of the product. The HCPCS code may be used later to generate a healthcare claim, as well as to initially verify that the product associated with the product identifier is a healthcare product.

At 415, method 400 verifies the identity of the user, for example, by communicating with the health plan server, such as server 101, to authenticate the user's insurance benefits eligibility and retrieve benefits information and recent claims history. At 420, method 400 evaluates benefits information and recent claims history. For example, the method may determine if there is a relevant diagnosis and/or prescription for the DME product in the recent claims history, and may further determine if the health plan benefits of the user covers the DME product.

At 425, method 400 determines if the item is covered by the user's health care benefits. Coverage of the item may be determined based on the HCPCS, the UPC, the health care benefits for the user, and the recent claims history for the user. For example, ten UPCs may be associated with one HCPCS code, but three of the UPCs may for some reason not be covered despite having an associated HCPCS code. As another example, the health care benefits may cover a product, but if the user has not received a prescription for the product or a relevant diagnosis, then the benefits may not cover the purchase. If the item is covered ("YES"), method 400 proceeds to 430. At 430, method 400 calculates the out-of-pocket cost of the item for the user. At 435, method 400 displays the calculated cost for the user. In some examples, the user may manually input the listed retail price of the DME product in order to obtain the out-of-pocket cost of the product, or method 400 may extract the listed retail price of the DME product from the webpage associated with the URL input at 405. Method 400 then proceeds to 455.

Referring again to 425, if the item is not covered ("NO"), method 400 proceeds to 440. At 440, method 400 determines if the item is a qualified expense for a Health Savings Account (HSA) or another similar medical savings account. If the item is not HSA qualified ("NO"), method 400 proceeds to 445. At 445, method 400 displays an alert that the product is not a qualified health expense. No coupon is generated, and method 400 returns.

However, referring again to 440, if the item is HSA qualified ("YES"), method 400 proceeds to 450. At 450, method 400 recommends use of the HSA account. For example, the method may display an indication that the product is not covered by the health care benefits but is HSA qualified. Method 400 then proceeds to 455.

At 455, method 400 determines if a purchase is indicated. For example, if the user decides to purchase the item and utilize the HSA account or the healthcare benefits, the user may indicate, via the application on the user device, to order the item for purchase. If a purchase is not indicated ("NO"), method 400 returns. However, if a purchase is indicated ("YES"), method 400 proceeds to 457.

At 457, method 400 optionally receives a pre-payment of the out-of-pocket cost from the user. For example, as discussed hereinabove with regard to FIG. 2, in some examples the user may opt to pre-pay the out-of-pocket cost for the healthcare item.

Continuing at 460, method 400 records the expense against the deductible. Continuing at 465, method 400 generates a digital coupon that administers healthcare benefits for the user. In some examples, the coupon may comprise a unique voucher entitling the holder to a discount for a particular product based on the healthcare benefits of the holder, while in other examples, the coupon may comprise a voucher that functions as a proof-of-purchase to count against a deductible. The coupon may be generated with a unique code or a coupon code intended for single use. Such a generated coupon is available only for designated member use. To that end, the coupon may be authenticated in real-time to a single member or user. If the item is not covered but is HSA qualified, the generated coupon may be used as a proof-of-purchase. If the item is covered, the generated coupon may be used to discount the item based on the user's coverage.

At 470, method 400 displays the coupon. For example, the coupon may be displayed via the display subsystem 125 of the user device 121 such that the user may obtain the coupon code for the coupon to redeem when purchasing the healthcare product from the online marketplace. As discussed above, the coupon may comprise a coupon code comprising an alphanumeric code, as a non-limiting example, that the user may input during checkout at the online marketplace to obtain the discount or validate the proof-of-purchase. If the user pre-payed at 457, then the discount is for the full listed retail price of the healthcare item. If the user did not pre-pay at 457, the discount reduces to the listed retail price to the out-of-pocket cost for the user calculated at 430. Method 400 then returns.

In one embodiment, a method comprises: responsive to a selection of a healthcare product input by a user, automatically determining if the healthcare product is a qualified healthcare expense; calculating an out-of-pocket cost to the user of the healthcare product based on a health insurance plan of the user; and generating a coupon for the healthcare product that discounts a retail cost of the healthcare product to the out-of-pocket cost responsive to a merchant accepting the coupon.

In a first example of the method, the user inputs the selection of the healthcare product by scanning, with a camera, a barcode of the healthcare product. In a second example of the method optionally including the first example, the method further comprises mapping a Universal Product Code (UPC) obtained from the barcode to a Healthcare Common Procedure Coding System (HCPCS) code. In a third example of the method optionally including one or more of the first and second examples, automatically determining if the healthcare product is a qualified healthcare expense is at least partially based on one or more of the UPC and the HCPCS code. In a fourth example of the method optionally including one or more of the first through third examples, the user inputs the selection of the healthcare product by providing a URL pointing to a product page for the healthcare product. In a fifth example of the method optionally including one or more of the first through fourth examples, automatically determining if the healthcare product is a qualified healthcare expense is based on the health insurance plan of the user and recent medical claims history for the user. In a sixth example of the method optionally including one or more of the first through fifth examples, the method further comprises displaying, via a display device, the coupon for scanning by the merchant. In a seventh example of the method optionally including one or more of the first through sixth examples, the method further comprises automatically generating a medical insurance claim for the healthcare product responsive to the merchant accepting the coupon. In an eighth example of the method optionally including one or more of the first through seventh examples, the coupon includes a unique code identifying the user, the healthcare product, and the out-of-pocket cost of the healthcare product.

In another embodiment, a system comprises: a server including a processor and a non-transitory memory storing one or more databases; a point-of-sale system for a merchant communicatively coupled to the server via a network; and a user device communicatively coupled to the server and including a processor and instructions stored in non-transitory memory that when executed cause the user device to generate a coupon for a healthcare product based on healthcare benefits information for a user of the user device retrieved from the one or more databases of the server; wherein the server is configured with instructions in the non-transitory memory that when executed cause the server to automatically generate a medical claim for the healthcare product responsive to receiving an indication from the point-of-sale system that the coupon is scanned by the point-of-sale system.

In a first example of the system, the user device is further configured with instructions stored in non-transitory memory that when executed cause the user device to automatically determine if the health-related product is a qualified healthcare expense responsive to receiving a selection by the user of the health-related product. In a second example of the system optionally including the first example, the user device further comprises a camera, and receiving the selection by the user of the health-related product comprises receiving, via the camera, an image of a barcode of the health-related product. In a third example of the system optionally including one or more of the first and second examples, the user device is further configured with instructions stored in non-transitory memory that when executed cause the user device to process the image of the barcode to obtain a Universal Product Code (UPC) from the barcode, and map the UPC to a Healthcare Common Procedure Coding System (HCPCS) code for the health-related product, wherein automatically determining if the health-related product is a qualified healthcare expense is based on one or more of the UPC and the HCPCS code. In a fourth example of the system optionally including one or more of the first through third examples, the user device further comprises a display device and the point-of-sale system includes a barcode scanner, wherein the coupon is displayed via the display device and wherein the coupon displayed on the display device is scanned by the barcode scanner. In a fifth example of the system optionally including one or more of the first through fourth examples, the user device is further configured with instructions in non-transitory memory that when executed cause the user device to calculate an out-of-pocket cost to the user of the health-related product based on the healthcare benefits information for the user, wherein the coupon discounts a retail cost of the health-related product to the out-of-pocket cost. In a sixth example of the system optionally including one or more of the first through fifth examples, the medical claim for the health-related product enables a transfer of an amount of funds to the merchant, the amount of funds based on a difference between the retail cost and the out-of-pocket cost.

In yet another embodiment, a method comprises receiving, from a user, a selection of a health-related product, determining whether the health-related product is a qualified healthcare expense, calculating an out-of-pocket cost to the user of the health-related product based on a health insurance plan of the user, generating and displaying a coupon for the health-related product if the health-related product is a qualified healthcare expense, wherein the coupon discounts a retail cost of the health-related product to the out-of-pocket cost responsive to a merchant accepting the coupon, and displaying an alert that the health-related product is not a qualified health expense and not generating the coupon for the health-related product if the health-related product is not a qualified healthcare expense.

In a first example of the method, determining whether the health-related product is a qualified healthcare expense comprises evaluating the health insurance plan of the user to determine if the health insurance plan provides coverage for the health-related product, and evaluating recent medical claims associated with the user to determine if there is a relevant diagnosis or prescription for the health-related product. In a second example of the method optionally including the first example, the method further comprises mapping a Universal Product Code (UPC) obtained from a barcode of the health-related product to a Healthcare Common Procedure Coding System (HCPCS) code, wherein automatically determining if the health-related product is a qualified healthcare expense is at least partially based on the HCPCS code. In a third example of the method optionally including one or more of the first and second examples, the method further comprises displaying the out-of-pocket cost to the user, and generating the coupon responsive to receiving an indication from the user that the user will purchase the health-related product.

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein. For example, although the methods and systems are described hereinabove with regard to brick-and-mortar retail stores, it should be appreciated that the methods and systems may be implemented for online retail marketplaces without departing from the scope of the disclosure. As an illustrative and non-limiting example, a user may provide a URL for a product page on an online marketplace to the application, which may automatically retrieve and/or determine the HCPCS code and/or UPC for the product from the product page. The application may then generate a digital coupon that may be applied at checkout in the online marketplace.

The following claims particularly point out certain combinations and sub-combinations regarded as novel and non-obvious. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application.

Such claims, whether broader, narrower, equal, or different in scope to the original claims, are also regarded as included within the subject matter of the present disclosure.

The invention claimed is:

1. A method, comprising:
   receiving, via a processor of a user device, a selection of a health-related product input by a user via the user device;
   responsive to the selection of the health-related product input by the user, automatically communicating, to a health plan server via the processor, to authenticate a health insurance plan of the user and retrieve benefits information and recent medical claims history for the user from one or more databases of the health plan server;
   automatically determining, with the processor, if the health-related product is a qualified healthcare expense based on the retrieved benefits information and the retrieved recent medical claims history for the user;
   calculating, with the processor, an out-of-pocket cost to the user of the health-related product based on the health insurance plan of the user retrieved from the one or more databases of the health plan server;
   generating, with the processor, a coupon for the health-related product that discounts a retail cost of the health-related product at a merchant to the out-of-pocket cost responsive to the merchant accepting the coupon via a merchant computing system, wherein a difference between the retail cost and the out-of-pocket cost charged to the user comprises an amount covered by the health insurance plan, wherein the coupon includes a unique code that identifies the user, the health-related product, and the out-of-pocket cost; and
   automatically generating, with the processor, a medical insurance claim for the health-related product responsive to receiving an indication from the merchant computing system indicating the merchant accepts the coupon, wherein the merchant computing system does not communicate with the health plan server to authenticate the health insurance plan of the user.

2. The method of claim 1, wherein the user inputs the selection of the health-related product by scanning, with a camera of the user device, a barcode of the health-related product.

3. The method of claim 2, further comprising mapping, with the processor, a Universal Product Code (UPC) obtained from the barcode to a Healthcare Common Procedure Coding System (HCPCS) code.

4. The method of claim 3, wherein automatically determining if the health-related product is a qualified healthcare expense is at least partially based on one or more of the UPC and the HCPCS code.

5. The method of claim 1, wherein the user inputs the selection of the health-related product by providing a URL pointing to a product page for the health-related product.

6. The method of claim 1, wherein automatically determining if the health-related product is a qualified healthcare expense based on the retrieved benefits information of the user and the recent medical claims history for the user comprises determining, with the processor, if there is a relevant diagnosis or prescription for the health-related product in the recent medical claims history, and determining, with the processor, if the health-related product is covered by the health insurance plan according to the retrieved benefits information.

7. The method of claim 1, further comprising displaying, via a display device of the user device, the coupon for scanning by the merchant.

8. The method of claim 1, wherein the health-related product comprises durable medical equipment.

9. The method of claim 1, further comprising determining that the user has pre-paid the out-of-pocket cost for the health-related product, and adjusting the coupon to cover the retail cost of the health-related product.

10. A system, comprising:
    a server including a processor and a non-transitory memory storing one or more databases;
    a point-of-sale system for a merchant communicatively coupled to the server via a network; and
    a user device communicatively coupled to the server and including a processor and instructions stored in non-transitory memory that when executed cause the user device to:
      receive, from a user of the user device, a selection of a health-related product available for sale by the merchant;
      receive, from the user, a retail price of the health-related product at the merchant;
      automatically retrieve, from the one or more databases of the server, healthcare insurance benefits information for the user;
      automatically determine that the health-related product is a qualified healthcare expense based on the healthcare insurance benefits information;
      generate a coupon for the health-related product that discounts the retail cost of the health-related product to an out-of-pocket cost for the user according to the healthcare insurance benefits information, wherein a difference between the retail cost and the out-of-pocket cost comprises an amount covered by a health insurance plan for the user, wherein the coupon includes a unique code that identifies the user, the health-related product, and the out-of-pocket cost;
    wherein the server is configured with instructions in the non-transitory memory that when executed cause the server to automatically generate a medical claim for the health-related product responsive to receiving an indication from the point-of-sale system that the coupon is scanned by the point-of-sale system; and
    wherein the point-of-sale system for the merchant automatically discounts the retail cost of the health-related product to the out-of-pocket cost after scanning the coupon.

11. The system of claim 10, wherein the user device is further configured with instructions stored in non-transitory memory that when executed cause the user device to automatically retrieve, from the one or more databases of the server, recent claims history for the user, and automatically determine if the health-related product is the qualified healthcare expense responsive to receiving the selection by the user of the health-related product by determining whether the recent claims history includes a relevant diagnosis or prescription for the health-related product.

12. The system of claim 10, wherein the user device further comprises a camera, and wherein receiving the selection by the user of the health-related product comprises receiving, via the camera, an image of a barcode of the health-related product.

13. The system of claim 12, wherein the user device is further configured with instructions stored in non-transitory memory that when executed cause the user device to process the image of the barcode to obtain a Universal Product Code (UPC) from the barcode, and map the UPC to a Healthcare Common Procedure Coding System (HCPCS) code for the health-related product, wherein automatically determining if the health-related product is a qualified healthcare expense is based on one or more of the UPC and the HCPCS code.

14. The system of claim 10, wherein the user device further comprises a display device and wherein the point-of-sale system includes a barcode scanner, wherein the coupon is displayed via the display device and wherein the coupon displayed on the display device is scanned by the barcode scanner.

15. The system of claim 10, wherein the user device is further configured with instructions in non-transitory memory that when executed cause the user device to calculate the out-of-pocket cost to the user of the health-related product based on the healthcare insurance benefits information for the user, wherein the coupon discounts the retail cost of the health-related product to the out-of-pocket cost.

16. The system of claim 15, wherein the medical claim for the health-related product enables a transfer of an amount of funds to the merchant, the amount of funds based on a difference between the retail cost and the out-of-pocket cost.

17. A method, comprising:
  receiving, at a processor of a user device from a user via the user device, a selection of a health-related product;
  determining, with the processor, whether the health-related product is a qualified healthcare expense;
  determining, with the processor, whether the health-related product is covered by a health insurance plan of the user;
  calculating, with the processor, an out-of-pocket cost to the user of the health-related product based on the health insurance plan of the user;
  generating, with the processor, and displaying, via a display device of the user device, a customized coupon for the health-related product if the health-related product is a qualified healthcare expense and covered by the health insurance plan, wherein the customized coupon is customized and unique to the user and discounts a retail cost of the health-related product to the out-of-pocket cost responsive to a merchant accepting the customized coupon, wherein a difference between the retail cost and the out-of-pocket cost comprises an amount covered by the health insurance plan;
  automatically generating, with the processor, a medical insurance claim for the health-related product responsive to receiving an indication from a merchant computing system indicating the merchant accepts the customized coupon, wherein the merchant computing system does not authenticate the health insurance plan of the user;
  generating, with the processor, and displaying, via the display device, a second customized coupon for the health-related product if the health-related product is a qualified healthcare expense and is not covered by the health insurance plan, wherein the second customized coupon is unique to the user and validates a proof-of-purchase for reimbursement from a health savings account for the user; and
  displaying, via the display device, an alert that the health-related product is not a qualified health expense and not generating the customized coupon or the second customized coupon for the health-related product if the health-related product is not a qualified healthcare expense.

18. The method of claim 17, wherein determining whether the health-related product is a qualified healthcare expense comprises evaluating, with the processor, recent medical claims associated with the user to determine if there is a relevant diagnosis or prescription for the health-related product.

19. The method of claim 17, further comprising mapping, with the processor, a Universal Product Code (UPC) obtained from a barcode of the health-related product to a Healthcare Common Procedure Coding System (HCPCS) code, wherein automatically determining if the health-related product is a qualified healthcare expense is at least partially based on the HCPCS code.

20. The method of claim 17, further comprising displaying, via the display device, the out-of-pocket cost to the user, and generating, with the processor, the customized coupon responsive to receiving an indication from the user that the user will purchase the health-related product.

\* \* \* \* \*